US00PP37392P2

(12) United States Plant Patent
Snijder

(10) Patent No.: US PP37,392 P2
(45) Date of Patent: Apr. 28, 2026

(54) ***PELARGONIUM* PLANT NAMED 'PEQZ0108'**

(50) Latin Name: ***Pelargonium* x *interspecific***
Varietal Denomination: PEQZ0108

(71) Applicant: SYNGENTA CROP PROTECTION AG, Basel (CH)

(72) Inventor: Ronald Christiaan Snijder, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 19/371,062

(22) Filed: Oct. 28, 2025

(51) Int. Cl.
*A01H 5/02* (2018.01)
*A01H 6/42* (2018.01)

(52) U.S. Cl.
USPC ..... Plt./324
CPC ..... *A01H 6/425* (2018.05)

(58) Field of Classification Search
USPC ..... Plt./324
CPC ..... A01H 5/02
See application file for complete search history.

*Primary Examiner* — Kent L Bell
(74) *Attorney, Agent, or Firm* — Dale Skalla

(57) ABSTRACT

A new *Pelargonium* plant named 'PEQZ0108' particularly distinguished by large white colored inflorescences with a red spot in the middle of the floret above medium green foliage, on a large mounding plant.

1 Drawing Sheet

Latin name of the genus and species of the plant claimed: *Pelargonium* x interspecific.

Varietal denomination: 'PEQZ0108'.

BACKGROUND OF THE NEW PLANT

The present invention comprises a new *Pelargonium*, botanically known as *Pelargonium* x interspecific, and hereinafter referred to by the variety name 'PEQZ0108'

'PEQZ0108' is a product of a planned breeding program. The new cultivar 'PEQZ0108' has large white colored inflorescences with a red spot in the middle of the floret above medium green foliage, on a large mounding plant.

'PEQZ0108' originates from a hybridization in a controlled breeding program made in May 2019 in a greenhouse in Enkhuizen, The Netherlands. The female parent was an unpatented plant of *Pelargonium* x interspecific parentage identified as 'PEZBE5098-6V' with very large light green foliage when compared to 'PEQZ0108'.

The male parent of 'PEQZ0108' was an unpatented, proprietary plant of *Pelargonium* x interspecific parentage, identified as 'PEZBE5079-24V' with a paler colored lower half of the petals when compared to 'PEQZ0108'. The resultant seed was sown in December 2019.

'PEQZ0108' was selected as one flowering plant within the progeny of the stated cross in May 2020 in a greenhouse in Enkhuizen, The Netherlands.

The first act of asexual reproduction of 'PEQZ0108' was accomplished when vegetative stem cuttings were propagated from the initial selection in July 2020 in a greenhouse in Enkhuizen, The Netherlands.

BRIEF SUMMARY OF INVENTION

Horticultural examination of plants grown from cuttings of the plant initiated in July 2020 in Enkhuizen, The Netherlands and continuing thereafter, has demonstrated that the combination of characteristics as herein disclosed for 'PEQZ0108' are firmly fixed and are retained through successive generations of asexual reproduction.

'PEQZ0108' has not been observed under all possible environmental conditions. The phenotype may vary significantly with variations in environment such as temperature, light intensity, and day length.

A Plant Breeder's Right for this cultivar has not yet been applied for. 'PEQZ0108' has not been made publicly available prior to the effective filing date of this application, notwithstanding any disclosure that may have been made less than one year prior to the effective filing date of this application by the inventor or another who obtained 'PEQZ0108' directly from the inventor.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

The accompanying photographic drawings show typical flower and foliage characteristics of 'PEQZ0108' with colors being as true as possible with an illustration of this type.

Figure 1:
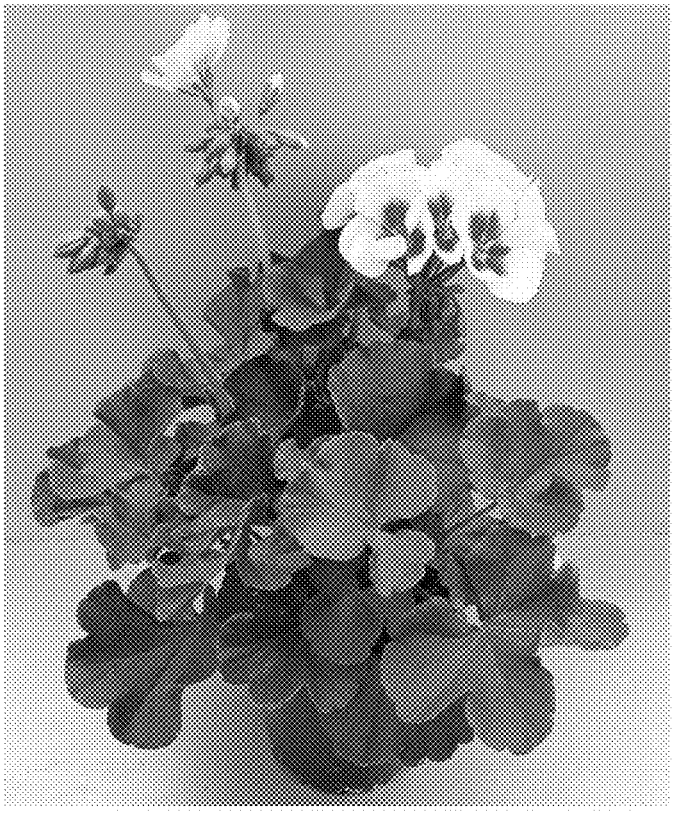
Figure 2:
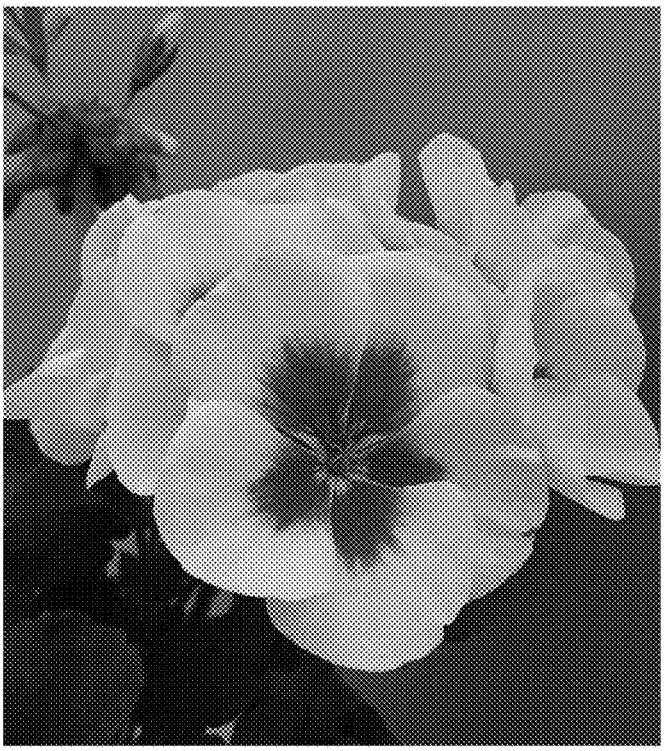

The photographic drawing shows in FIG. 1, one flowering plant of the new variety and in FIG. 2, a close-up of an inflorescence.

DETAILED BOTANICAL DESCRIPTION

The plant descriptions and measurements were taken in Enkhuizen, The Netherlands in May 2023 under natural light. These plants were approximately 12 weeks old and were grown in a 13 cm pot, in a greenhouse trial. The photographs were taken in May 2023.

Color references are made to The Royal Horticultural Society Colour Chart (R.H.S.) of 2015.

TABLE 1

DIFFERENCES BETWEEN THE NEW VARIETY 'PEQZ0108' AND A MOST SIMILAR VARIETY

| | 'PECZ0003' (U.S. Plant Pat. No. 23,509) | 'PEQZ0108' |
|---|---|---|
| Plant height including umbel: | Smaller (Approximately 24 cm) | Larger (Approximately 31-35 cm) |
| Color of pollen: | Orange (About RHS 25A) | Dark orange - brown (About RHS 171B to 171D) |

Plant:

*Form, growth and habit.*—Mounding growth habit.
*Plant height.*—19-23 cm.
*Plant height (inflorescence included).*—31-35 cm.
*Plant width.*—32-35 cm.

Roots:

*Number of days to initiate roots.*—15-18 days at about 22 degrees C.
*Number of days to produce a rooted cutting.*—21-23 days at 22 degrees C.
*Type.*—Fine, fibrous, free branching.
*Color.*—RHS N155B but whiter.

Foliage:

*Variegation.*—None.
*Immature leaf, color upper surface.*—Between RHS 137C and RHS 137D.
*Immature leaf, lower surface.*—RHS 138B.
*Mature leaf, color upper surface.*—Between RHS 137B and RHS 137C.
*Mature leaf, color lower surface.*—Between RHS 138A and RHS 138B.
*Length.*—6-11 cm.
*Width.*—7-12 cm.
*Shape.*—Cordate.
*Base shape.*—Cordate.
*Sinus of mature leaf.*—Medium.
*Leaf base openness.*—Variable, immature leaves wide open, mature leaves open.
*Apex shape.*—Obtuse.
*Margin.*—Slightly serrate.
*Texture upper side.*—Hirsute.
*Texture lower side.*—Hirsute.
*Leaf zonation color.*—None.
*Color of veins, upper surface.*—RHS 137C, indistinct.
*Color of veins, lower surface.*—RHS 138B, indistinct.
*Pattern of veining.*—Palmate.
*Petiole color.*—Between RHS 143B and RHS 143C.
*Petiole length.*—5-9 cm.
*Diameter of petiole.*—0.2-0.4 cm.
*Texture.*—Pilose, hirsute, glandular hairs.

Stem:

*Quantity of branches.*—5-9.
*Color of stem.*—Between RHS 143B and RHS 143C.
*Anthocyanin coloration of stem.*—None.
*Length of stem.*—10-18 cm.
*Diameter.*—0.5 cm.
*Length of internodes.*—2-5 cm.
*Texture.*—Sparsely hirsute, pilose, glandular hairs.

Peduncle:

*Color of peduncle.*—Between RHS 143B and 143C.
*Length of peduncle.*—12-17 cm.
*Peduncle diameter.*—0.3-0.5 cm.
*Texture.*—Hirsute, glandular hairs.
*Anthocyanin coloration of peduncle.*—Little to no anthocyanin coloration.

Pedicel:

*Color of pedicel.*—Between RHS 143B and RHS 143C.
*Length of pedicel.*—1.5-2.5 cm.
*Diameter of pedicel.*—0.2 cm.
*Texture.*—Sparsely pilose, glandular hairs.
*Pedicel swelling.*—Minimal to no swelling.

Bud (just before opening):

*Color.*—RHS 49D.
*Length.*—1.5-2 cm.
*Width.*—0.6-1 cm.
*Shape.*—Elliptical.

Inflorescence:

*Type.*—Umbel; semi-spherical or nearly semi-spherical.
*Lastingness of individual flowers.*—7-9 days at 18° C. temperature.
*Number of inflorescences per plant.*—6-12, with 5-12 immature umbels in various stages.
*Average total number of buds.*—25-35.
*Fragrance.*—None.
*Umbel diameter.*—11-13 cm.
*Umbel depth.*—6-8 cm.

Corolla:

*Form.*—Single.
*Number of petals.*—5.
*Diameter of flower.*—4.5-5.3 cm.
*Depth of flower.*—1-2 cm.
*Side view shape.*—Concave.
*Color upper petals, upper surface.*—Upper half RHS N155B, coloring to RHS 58B on the lower half.
*Color upper petals, lower surface.*—RHS N155B.
*Length of upper petals.*—2.3-2.7 cm.
*Width of upper petals.*—2.7-3.0 cm.
*Color lower petals, upper surface.*—Upper half RHS N155B, coloring to RHS 58B on the lower half.
*Color lower petals, lower surface.*—RHS N155B.
*Markings om upper petals.*—Yes, the lower half is colored RHS 58B and there are some stripes RHS 58B on the base.
*Markings on lower petals.*—Yes, the lower half is colored RHS 58B and there are some stripes RHS 58B on the base.
*Length of lower petals.*—2.3-2.7 cm.
*Width of lower petals.*—2.7-3.0 cm.
*Petal shape.*—Obovate to spathulate.
*Apex shape.*—Rounded.
*Margin.*—Entire.
*Base.*—Attenuate.
*Petal texture.*—Papillose on both surfaces.

Calyx:

*Number of sepals.*—5.
*Color of sepals.*—RHS 143B.
*Length of sepals.*—1.2-1.3 cm.
*Width of sepals.*—0.2-0.6 cm.
*Sepal shape.*—Lanceolate to linear.
*Apex shape.*—Acute.
*Margins.*—Mostly fused.
*Texture, upper surface.*—Glabrous, hirsute.
*Lower surface.*—Glandular hairs, hirsute.
*Sepal flexing.*—Mostly unflexed sepals. The narrowest sepals might flex moderately.

Reproductive organs:

Gynoecium:

*Pistil*.—RHS 62D.

*Length*.—0.5 cm.

*Style color*.—RHS 62D.

*Style length*.—0.3 cm.

*Stigma color*.—RHS 62D.

*Ovary color*.—RHS 143D.

*Ovary length*.—0.4-0.6 cm.

*Ovary diameter*.—0.3 cm.

Androecium:

*Number of stamens*.—5 with 2 staminodes.

*Color of filaments*.—RHS 157D.

*Length filaments*.—0.4-0.8 cm.

*Anther color*.—RHS 155A.

*Length of anthers*.—0.2-0.4 cm.

*Color of pollen*.—About RHS 171B to 171D.

*Pollen amount*.—Scarce.

*Fertility/seed set*.—Has not been determined to date.

*Disease/pest resistance*.—Has not been determined to date.

What is claimed is:

1. A new and distinct variety of *Pelargonium* plant named 'PEQZ0108' substantially as illustrated and described herein.

* * * * *